United States Patent [19]
Zisapel

[11] Patent Number: 6,048,888
[45] Date of Patent: Apr. 11, 2000

[54] METHOD AND PHARMACEUTICAL FORMULATION FOR TREATING BENIGN PROSTATIC HYPERPLASIA

[75] Inventor: Nava Zisapel, Tel Aviv, Israel

[73] Assignee: Neurim Pharamaceuticals (1991) Ltd., Tel-Aviv, Israel

[21] Appl. No.: 08/976,508

[22] Filed: Nov. 24, 1997

Related U.S. Application Data

[60] Division of application No. 08/111,014, Aug. 24, 1993, Pat. No. 5,750,557, which is a continuation-in-part of application No. 07/864,684, Apr. 7, 1992, abandoned.

[30] Foreign Application Priority Data

Mar. 13, 1993 [IL] Israel ........................................ 105240

[51] Int. Cl.$^7$ ................................................. A61K 31/405
[52] U.S. Cl. .............................................................. 514/415
[58] Field of Search ............................................ 514/415

[56] References Cited

U.S. PATENT DOCUMENTS

| | | | |
|---|---|---|---|
| 4,600,723 | 7/1986 | Short et al. | 514/416 |
| 4,654,361 | 3/1987 | Samples et al. | 514/419 |
| 4,945,103 | 7/1990 | Cohen | 514/419 |
| 5,196,435 | 3/1993 | Clemens et al. | 514/415 |

FOREIGN PATENT DOCUMENTS

| | | |
|---|---|---|
| 0330652 | 8/1989 | European Pat. Off. . |
| 0518468 | 12/1992 | European Pat. Off. . |
| 8807370 | 10/1988 | WIPO . |
| 8904659 | 6/1989 | WIPO . |
| 9100095 | 1/1991 | WIPO . |

OTHER PUBLICATIONS

Laudon et al., Neuroendocrinology, 48, 577, 1988.
Chemical Abstracts 97: 66816e (1982).
Yamada, Chem. Pharm. Bull., vol. 40, pp. 1066–1068, 1988.
Laudon et al., J. Endocrinol., vol. 116, No. 1, 1988, pp. 43–53.
Moguilevsky et al., Proc. Soc. Exp. Biol. Med., vol. 151, No. 4, 1976, pp. 663–666.
Srivilai et al., J. Pineal Res., vol. 6, No. 2, 1989, pp. 111–119.
Horst et al., Horm. Metabol. Res., vol. 14, p. 54, 1982.
Guess, Epidemiologic Reviews, vol. 14, pp. 131 et seq., 1992.
Walsh et al., J. Clinical Investigation, vol. 72, Nov. 1983, pp. 1772–1777.

*Primary Examiner*—Jerome D. Goldberg
*Attorney, Agent, or Firm*—Rothwell, Figg, Ernst & Kurz

[57] ABSTRACT

Benign prostatic hyperplasia (BPH) in male humans is treated by administering to a male patient in which such condition has been diagnosed, an effective BPH treating amount within the range of from 1 ng to 80 mg of melatonin, which may be in the form of a pharmaceutical formulation for use in treating BPH, which comprises, in combination a carrier, diluent or adjuvant, (1) an effective BPH treating amount of melatonin; and optionally (2) antiandrogens, antiestrogens, growth hormones and/or inhibitors of prostatal testosterone reductase; and/or (3) oxazepam or other melatonin receptor profile modifier.

4 Claims, 1 Drawing Sheet

METHOD AND PHARMACEUTICAL FORMULATION FOR TREATING BENIGN PROSTATIC HYPERPLASIA

This is a divisional of application Ser. No. 08/111,014, filed Aug. 24, 1993, now U.S. Pat. No. 5,750,557 which is a continuation-in-part of Ser. No. 07/864,684, filed Apr. 7, 1992, now abandoned.

FIELD OF THE INVENTION

The present invention relates to a method for treating benign prostatic hyperplasia (BPH) and to a pharmaceutical formulation for this purpose.

BACKGROUND OF THE INVENTION

Melatonin is the principal hormone secreted by the pineal gland in all vertebrates. In all mammals studied to date, including humans, a nocturnal rise in the production of melatonin by the pineal gland is evident, regardless of whether the mammals are nocturnal or diurnal, and conversely, melatonin production by the body is acutely suppressed by light. Melatonin is involved in the coordination of photoperiod and physiological processes, e.g. in animals which use changes in the photoperiod to time their thermoregulation and reproduction, temporal signals to the thermoregulatory and reproductive systems are controlled by the daily rhythm in the duration of melatonin during the dark phase. Numerous studies have shown that melatonin has a potent influence on gonadal activity.

The timing of melatonin administration has been shown to be crucial for its biological activities. E.g., while in the case of rats whose circadian rhythms are disrupted or arrhythmic in constant light, as well as in the case of rats free running in constant darkness, their rhythms are synchronized by daily melatonin injections, by contrast it has been found that continuous availability of melatonin in circulation, or injection of melatonin in the morning, sometimes prevents gonodal responses to melatonin in the afternoon. The inventor has shown, e.g. in Zisapel et al, Neuroendocrinology 40: 102 (1985), that the inhibition by melatonin of the stimulated release of dopamine from rat hypothalamus, was highest in the early photophase and lowest in the early afternoon.

The ability of the animals or humans to respond to the melatonin signal may depend upon melatonin receptors. Thus, it has been shown that in rats and Syrian hamsters, under a daily schedule of 14 hours light/10 hours darkness, the densities of melatonin binding sites in discrete brain areas (hypothalamus, medulla-pons and hippocampus) vary significantly over the 24-hour period with different patterns and phases, but no such variation was observed in other brain areas (striatum, parietal cortex, cerebellum). Only a partial overlap existed between the timing of peaks or troughs of melatonin binding sites and crests or nadirs in tissue melatonin content, so that the rhythms in melatonin binding sites may not be due to autoregulation of the receptors by the endogenous hormone. In this connection, it has also been shown that injection of exogenous melatonin to young rats or hamsters in the morning or late afternoon did not affect the density or diurnal variations in melatonin binding sites in most brain areas; in the hippocampus and midbrain, melatonin injected in the morning prevented the usual late afternoon rise in melatonin binding sites, whereas melatonin injected in the late afternoon suppressed the nocturnal rise in melatonin binding sites in the midbrain only.

It is also known that exogenously administered melatonin when administered in the late afternoon elicits antigonadal responses and decreases serum concentrations of testosterone in hamsters and immature rats, whereas in pinealectomized hamsters held in long days, the duration of melatonin administration is crucial in that 10 h infusions in long days elicit gonadal regression in hamsters while after previous exposures to short days, 4–6 hour infusions of melatonin stimulated the gonads.

It is further known that in several species, including rats and humans, night-time melatonin production in the pineal gland declines with age. Moreover, a decline in 24 hour mean values and loss of circadian variations in melatonin binding sites was found to occur in discrete areas of the aged rat brain, as indicated by use of $^{125}$I-melatonin as a probe (Laudon et al, Neuroendocrinology, 48; 577, 1988). While the melatonin rhythm might not be the cause for the $^{125}$I-melatonin binding rhythms recorded in the rat brain, the possibility exists that the decline in amplitude of the melatonin rhythm leads to the dispersal of phase, resulting in the obliteration of rhythmicity in melatonin binding sites in the brain. In other words, the age-related decrease in melatonin levels and binding site density may lead to a decline in the ability of the neuroendocrine system to respond to photoperiodic messages.

Melatonin has been given to human subjects intravenously or orally and no significant toxicity has been observed. Various studies have demonstrated a melatonin-mediated fatigue and sometimes depression or sleep. Melatonin may not be hypnotic but it alters the timing of the sleep-wake cycles through its effects on circadian organization, e.g., recent studies have indicated that timing of the nocturnal sleep gate is temporarily related to the nocturnal increase in melatonin excretion, The "opening" of the sleepiness gate may represent a critical accumulation of melatonin which activates somogenic structures in the brain.

The use of melatonin for various therapeutic purposes has been the subject of a number of patents and patent applications. Thus e.g., U.S. Pat. No. 4,600,723 discloses the administration of melatonin in order to alleviate or prevent the negative effects of disturbances in circadian rhythms of bodily performance and function, such as may occur in a change of work patterns from day to night shift, or in cases of jet lag.

Moreover, U.S. Pat. No. 4,654,361 discloses the administration of melatonin order to lower intraocular pressure in a human, where such pressure is abnormally high, while U.S. Pat. No. 4,945,103 discloses a method of treating premenstrual syndrome by administering melatonin at dosage levels sufficient to alleviate the symptoms.

PCT Patent Application No. WO 87/004032 describes compositions, for treating or preventing psoriasis, which contain melatonin or related compounds. PCT Patent Application No. WO 88/07370 discloses the administration of melatonin for the purpose of inhibiting ovulation in human females, thereby effecting contraception, as well as for preventing breast cancer in women. The use of melatonin or related compounds is disclosed in PCT Patent Application No. WO 89/04659, as a component in pharmaceutical compositions in order to counteract the effects of aging. European Patent Application No. 0330625A2 discloses the production of melatonin and analogs thereof, for various therapeutic purposes, including the administration of melatonin in combination with an azidothymidine for the treatment of AIDS.

My prior U.S. patent application Ser. No. 07/697,714, filed May 9, 1991, relates to a method for correcting a melatonin deficiency or distortion in the plasma melatonin level and profile in a human subject, and to a pharmaceutical controlled-release formulation, which contains melatonin.

The entire contents of U.S. Pat. Nos. 4,600,723, 4,654, 361, 4,945,103, PCT Patent Application No. WO 87/00432 PCT Patent Application No. WO 88/07370, PCT Patent Application No. WO 89/04659 and European Patent Application No. 0330625A2, and of my said prior U.S. Patent Application, are explicitly incorporated herein by reference.

The Prostate, Androgens and Melatonin

Although it is known that the volume of the seminal plasma is produced by the prostate, the seminal vesicles and the bulbourethral (Cowper's) glands, the specific biological function of the prostate gland is still unknown. Diseases caused by pathology of the prostate are some of the most common and devastating diseases in the human male. Abnormal overgrowth (hyperplasia) of the human prostate (BPH) occurs in over 80% of the male population before the age of 80 and 25% will require surgery at some time in order to alleviate urinary obstruction caused by this overgrowth (for review, see Oesterling, J. E., J. Andrology 12, 348–55, December 1991). The exact cause of BPH is not well defined, but is thought to occur as a result of epithelial-stromal interactions in the appropriate hormonal milieu, specifically, in the presence of androgens. Although prostatectomy is the current treatment of choice for BPH, medical therapies aimed at shrinking the enlarged gland are being developed as additional options.

Both the differentiation of the prostate gland and subsequent postnatal growth of the tissue are controlled by androgenic hormones synthesized in the testes, which are converted into dihydrotestosterone within the gland. Unregulated dihydrotestosterone action is believed to cause hyperplastic prostate growth. Androgen withdrawal has been shown to lead to programmed cell death (apoptosis) in the rat ventral prostate.

Testosterone deficiency leads to a rapid involution of the prostate, because androgen ablation inhibits the proliferation of the androgen-dependent prostatic glandular cells and induces these cells to undergo both cellular atrophy (i.e. decrease in cell height and secretory functions) and activation of a cascade of biochemical events, resulting in the energy-dependant programmed death of these cells. Thus, there are at least three cellular responses that androgens affect within the androgen-dependent prostatic glandular cells: secretion, proliferation and inhibition of death. The specific androgen moieties responsible for each of these responses within the prostate are not totally resolved. Quantitatively, the major circulating androgen in the blood is testosterone. Within the prostate, testosterone is rapidly converted to a series of metabolites, a major one being 5α-dihydrotestosterone (DHT). which is the active intracellular androgen in androgen-dependent prostatic glandular cells. It is known that Androgen metabolizing enzymes in the human BPH change t o a lower 3α hydroxysteroid reductase and a higher 3 ketosteroid 5α reductase when compared to normal tissue.

Recently developed methods for the treatment of BPH include e.g. chemical castration with luteinizing hormone-releasing hormone (LHRH) analogs resulting in androgen deprivation, but have the disadvantages of causing loss of testosterone-dependent functions such as muscle mass, libido and erection.

It is known that 5α reductase activity is elevated in prostatic stromal cells in BPH, and that treatment with 5α reductase inhibitors, decreases the size of the prostate in animals and humans suffering from BPH. Unlike castration, which reduces all androgens in the prostate, treatment with 5α reductase inhibitors lowers levels of DHT and its metabolites while increasing testosterone within the prostate. This large increase in prostatic testosterone could overcome some portion of the initial inhibition by the competitive 5α reductase inhibitors leading to incomplete inhibition of prostatal growth. In this respect it is noteworthy that melatonin does not increase circulating testosterone levels in humans. The mode of action of melatonin on prostatal development and growth may differ from that of 5α reductase inhibitors. Melatonin has been shown to stimulate 3α reductase activity but did not affect 5α reductase activity in BPH tissue samples (Horst and Adam, Horm. metab. Res. 14, 54, 1982) suggesting that melatonin could lower prostatic DHT levels by enhancing its conversion to 3α androstandiol.

Other methods, such as the use of non-steroidal antiandrogens which block testosterone mediated responses without suppressing testosterone levels, are still at the experimental stage.

Melatonin plays a major role in the control of reproductive physiology (reviewed by Tamarkin et al. Science 227, 714–720, 1985) especially in seasonal breeders, such as hamsters and sheep, in which it mediates the effects of short photoperiod on gonadal physiology. Certain parts of the brain, especially the hypothalamus, have been implicated as the sites of melatonin's antigonadal and neuroendocrine activities (Glass, Pin. Res. Rev. 6, 219–259, 1988). In the male rat, castration, or degeneration of the testicular Leidig cells, produced a marked decrease in melatonin binding sites particularly in the hypothalamus and hippocampus; this effect was reversed by injection of exogenous testosterone (Zisapel and Anis, Mol. Cell. Endocrinol. 60, 119–126, 1988). In the Syrian hamster, castration also led to a testosterone-reversible decrease in melatonin binding sites in the brain; this response was evident in animals maintained in short but not long days (Anis and Zisapel, Molec. Cell. Endocrinol. 76, 23–34, 1991.

It is further known that melatonin inhibits testicular testosterone synthesis in the rat (Peat and Kinson, Steroids 17, 251–264, 1971), decreases androgen synthesis in both testicular interstitial cells and tubules (Ellis, Endocrinology 90, 17–28, 1972), stimulates delta-4-reductase activity in the rat liver and hypothalamus (Frehn et al. J. Endocrinol. 60, 507–515, 1974), increases 5α-reductase of seminiferous tubules for both progesterone and testosterone (Ellis, Endocrinology 90, 17–28, 1972), increases adrenal secretion of reduced steroid metabolites in female rats (Ogle and Kitay, Neuroendocrinology 23, 113–120, 1977), and reduces accessory sex gland size in pinealectomized male rats kept in constant darkness without inhibiting testosterone metabolism (Shirama et al. J. Endocrinology 95, 87–94, 1982). Orally administered melatonin lowered ventral prostate and seminal vesicle weight and increase the 3β-hydroxysteroid reductase but not 5α reductase in the ventral prostate and seminal vesicles of pinealectomized rats (Horst et al. Experimentia 388, 968–970, 1982). The effects of melatonin on prostatic androgen receptors depends on the age of the animal and light cycle exposure (Moeller et al. Res. Exp. Med. 183, 157–165, 1983). Melatonin in vitro augments the luteinizing hormone or chorionic gonadotrophin induced increase in secretion of estrogen and progesterone from rat granulosa cells (Fiske et al. Endocrinology 114, 407–410, 1984), and stimulates the secretion of progesterone by human and bovine granulosa cells in vitro (Webley and Luck, J. Reprod. Fert. 78, 711–717, 1986; Webley et al. J. Reprod. Fert 84, 669–677, 1988).

It has been shown that subcutaneous administration of high doses (750 mcg.) of melatonin enhances regression of the ventral prostate gland in presence of exogenous testosterone in castrated rats (Debeljuk et al, Endocrinology 87, 1358–1360, 1970) and decreases the weight of both the testes and the ventral prostate gland in hypophysectomized animals (Debeljuk et al, Endocrinology 89, 1117–1119, 1971). (It may be noted in passing that the amount of melatonin equivalent to that administered to rats by Debeljuk et al, for administration to an 80 kg human, would be more than 200 mg.) Other studies have shown that oral administration of 16–40 mcg. per day delayed pubertal development of male and female rats, including prostate development in the males (Zisapel and Laudon, Eur. J. Pharmacol. 136, 259–60, 1987; Laudon et al, J. Endocrinology 116, 43–53, 1988).

It has never been suggested in the scientific literature that melatonin receptors are present in the prostate. Moreover, neither the scientific literature on the subject of melatonin, nor any of the above-mentioned Patents or published Patent Applications disclose or suggest the possibility of utilizing melatonin for treating BPH in humans.

SUMMARY OF THE INVENTION

The present invention provides in one aspect a method for treating benign prostatic hyperplasia (BPH) in male humans in which this condition exists, which comprises administering to a patient in which such condition has been diagnosed, an effective BPH treating amount within the range of from 1 ng to 80 mg of melatonin.

In another aspect, the invention relates to a pharmaceutical formulation for use in treating BPH, which comprises an effective BPH treating amount within the range of from 1 ng to 80 mg of melatonin, in combination with at least one pharmaceutically acceptable carrier, diluent or adjuvant.

In still another aspect, the invention relates to a pharmaceutical formulation for use in treating BPH, which comprises (1) an effective BPH treating amount within the range of from 1 ng to 80 mg of melatonin, and (2) a second active component which comprises at least one member of the group consisting of growth hormones, inhibitors of prostatal testosterone reductase, antiestrogens and antiandrogens, in combination with at least one pharmaceutically acceptable carrier, diluent or adjuvant.

DETAILED DESCRIPTION OF THE INVENTION

Figure 1:
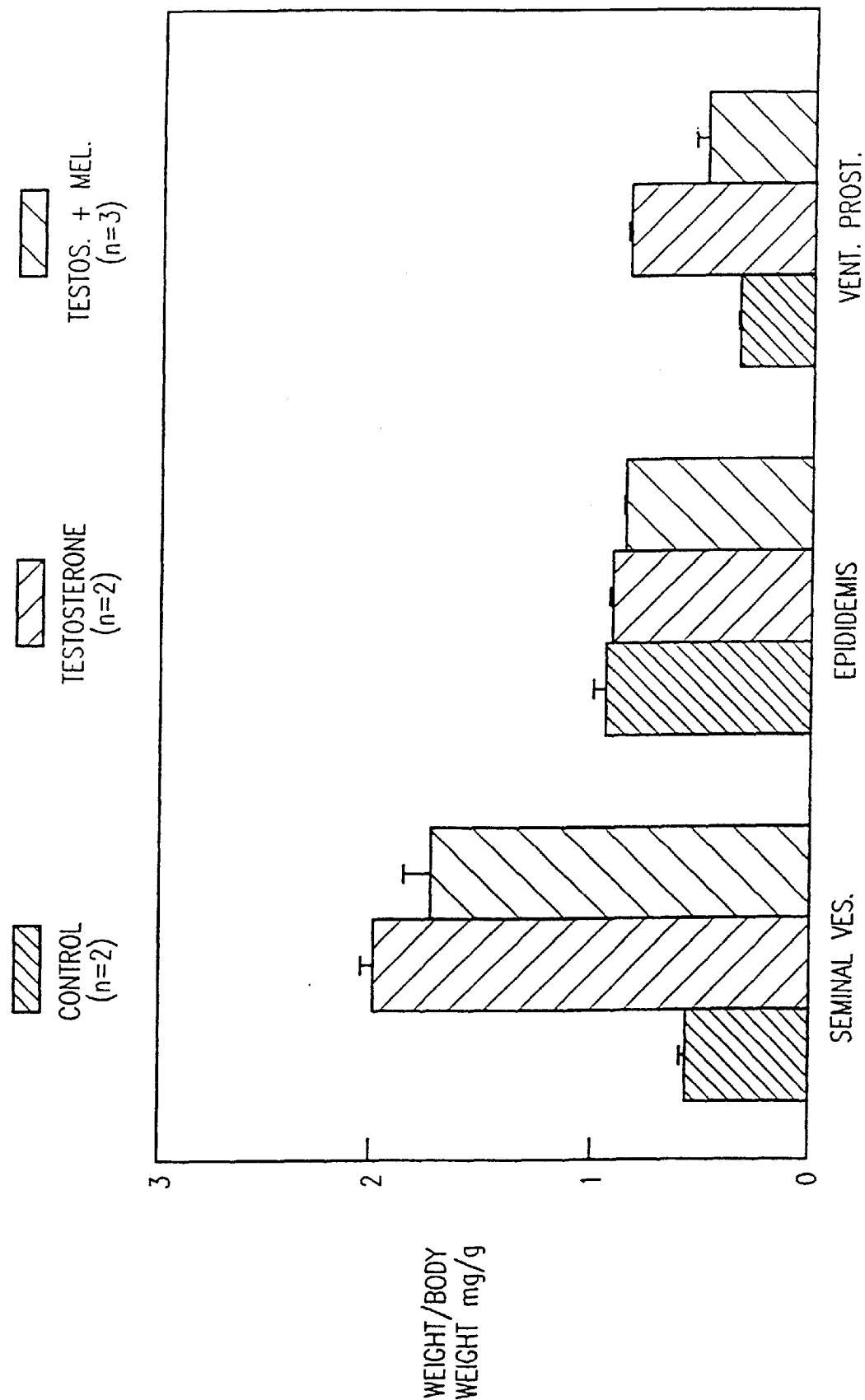
FIG. 1 shows the effect of testosterone, with or without melatonin, on the regrowth of certain accessory sex organs in castrated rats.

The formulation in accordance with the invention may be formulated for a mode of administration selected, e.g., from oral, parenteral, rectal and transdermal administration, and may contain, e.g., 1 ng–80 mg melatonin per dosage unit. Unit dosages may be administered e.g. once a day, for example in the morning, afternoon or evening, or twice daily, e.g. both morning and evening.

In a particular embodiment, the formulation according to the invention is in slow release form which may mimic the normal endogenous melatonin rhythm, but need not mimic the normal rhythm. In this embodiment, the melatonin may be in particulate form comprising coated particles and the desired release profile may then be achieved by at least one of the following characteristics, namely:

(a) by variation in the particle size of the melatonin;

(b) by use of at least two different coating materials which dissolve at different rates in the human body; and (c) by varying the thickness of coating material(s) whereby particulate melatonin coated with different thicknesses of coating material(s) dissolve at different rates in the human body.

In such an embodiment of the invention, the formulation may e.g. comprise particulate melatonin coated with at least one polymeric coating material, e.g. selected from natural and synthetic polymer coating materials.

The formulation of the invention will preferably be administered towards the end of the day, so that melatonin will be available in the system at the time of maximal responsiveness of the endocrine system thereto. Persons skilled in the pharmaceutical art will be able to formulate the controlled-release formulations of the present invention on the basis of the information given in the present specification, in conjunction with known principles for making pharmaceutical formulations. Moreover, administration of melatonin in accordance with the present invention includes the co-administration therewith of one or more substances which alter the phase position or shape of melatonin receptor profiles. A non-limiting example of such melatonin receptor profile modifiers is oxazepam, which may potentiate the response to melatonin by affecting the phase position of the receptors. In accordance with an embodiment of the invention at, least one such modifier, e.g. oxazepam, may be included in the pharmaceutical formulation of the invention.

EVIDENCE FOR CYTOPLASMIC MELATONIN RECEPTORS IN EPITHELIAL CELLS FROM HUMAN BENIGN HYPERPLASTIC PROSTATE TISSUE

Introduction

Since hormones are known to exert their effects through binding to receptor proteins in target organs, target cells for a given hormone should contain specific receptors for that particular hormone to be affected by it. The inventor has thus examined the presence of melatonin binding sites in human prostatic tissue specimens.

Two type of melatonin receptors have been described in the scientific literature: membrane-associated and cytosolic sites (for review see Zisapel, Journal of Neural Transmission, 73: 1 (1988). There is now presented evidence on the presence of cytosolic sites in epithelial but not stromal cells from the human prostate.

Method

Tissue specimens were obtained from prostate glands removed by open surgery from patients suffering from urinary obstruction due to benign prostatic hyperplasia. Epithelial and stromal cells were separated from the tissue by filtration through a stainless steel mesh. The cells were then washed with saline and collected by centrifugation (1000 g, 5 min). Histological staining followed by light-microscopic evaluation showed that the epithelial cell preparation contained over 80% epithelial cells and the stromal preparation contained mostly stromal cells, but also amorphic amyloid, smooth muscle cells, and residual epithelial cells (<10%). The two preparations were separately homogenized at 4° C. in 0.05 M Tris-HCl, pH 7.4. Each homogenate was spun at 100,000 g for 1 hour at 4° C. and the supernatant was removed with a Pasteur pipette. Melatonin binding was measured by incubating 300 microliters of supernatant containing ca. 20 mcg. protein with carrier-free $^{125}$I-melatonin at concentrations of 0–1 nM, for 1 hour at 37°

C. in the presence of 0.05% Triton X-100. After the incubation period, bound $^{125}$I-melatonin was separated from free $^{125}$I-melatonin by vacuum filtration using GFF glass fiber filters saturated with polyethylenimine. Protein concentrations were measured by the method of Lowry et al (J. Biol. Chem., 193: 265, 1951) using bovine serum albumin as a standard. Non-specific binding was determined by incubating the supernatant samples with the specified concentrations of $^{125}$I-melatonin, but in the presence of a vast excess (10 micromolar) nonradioactive melatonin. These experiments were repeated four times, using specimens from four different patients, with similar results.

Results

Specific binding of melatonin, defined by the difference in binding in the absence and presence of unlabelled melatonin, was detected in the supernatant from the epithelial cells of the human prostate, whereas binding in the stromal preparations was very low (Table 1). Analysis of the concentration dependencies of the binding, indicated saturable-high affinity binding with a dissociation constant of 0.6 nanomolar and a binding site density of 140 fmol/mg cytosol protein. The concentration of binding sites in the stromal cytosol was lower than that by approximately 10 x, and could represent binding to cytosol of the residual epithelial cells in the preparation.

TABLE 1*

Specific binding of $^{125}$I-melatonin to cytosol preparations from epithelial and stromal cells of human BPH tissue (4 patients).

| $^{125}$I-melatonin (concentration, nM) | 0 | 0.05 | 0.10 | 0.20 | 0.30 | 0.50 | 1.00 |
| --- | --- | --- | --- | --- | --- | --- | --- |
| Bound in Epithelial | 0 | 6.25 | 12.5 | 31.3 | 45.6 | 66.9 | 93.1 |
| Standard Deviation | 0.1 | 2.5 | 3.8 | 9.3 | 5.2 | 2.5 | 9.1 |
| Bound in Stromal | 0 | 0.6 | 2.5 | 3.7 | 4.3 | 8.8 | 16.2 |
| Standard Deviation | 0.2 | 0.3 | 0.6 | 0.7 | 1.2 | 2.5 | 4.4 |

*Mean and Standard Deviation values of binding (fmol/mg protein)

Conclusions

These results represent the first evidence of specific high-affinity melatonin binding in the prostate gland, and that the sites are cell type specific. Furthermore, melatonin responses in the prostate may be associated with cytosol receptors in the epithelial cells.

The experiments which follow are relevant to the method and formulation of the present invention.

IN VIVO EXPERIMENTS

Experiment 1

The effects of orally administered melatonin on androgen-dependent prostatal regrowth in adult castrated rats was investigated. Male rats (2.5 months old) were castrated under anesthesia. After 7 days, during which the average weight of the prostate decreased by ca. 60%, the rats were given daily for 4 days, a subcutaneous injection of either oil vehicle (control) or oil vehicle containing testosterone propionate (1 mg/kg body weight per day, at one hour before lights-off). The drinking water of a sub-group of half of the animals injected with testosterone contained 10 mg melatonin dissolved in 100 mcl. ethanol/liter water; it was estimated that each rat in the sub-group receiving melatonin had an intake of approximately 4 ml solution, i.e. about 40 mcg melatonin per day. In order to determine the weight of the relevant organs, the rats were sacrificed at the end of the 4 days following the first 7 days. The results are illustrated in FIG. 1, which shows the effect of testosterone, with or without melatonin, in the present experiment. As is apparent from the illustration, whereas testosterone increased the weight of the seminal vesicles and ventral prostate in the castrated animals but had no effect on the epididemis, melatonin in presence of testosterone prevented the testosterone-mediated regrowth of the prostate but did not significantly affect regrowth of the seminal vesicles and had hardly any effect on the epididemis. These studies indicate a direct inhibitory effect of orally administered melatonin on prostatal growth in adult rats, contrary to the dogma that melatonin can affect the pubertal development of the rat only during the first (prepubertal) 40 days of life (Lang et al. Endocrinology, 112, 1578–1584, 1983).

Experiment 2

In a placebo-controlled continuing study on the effect of oral administration at about 10 p.m. of 5 mg melatonin/day in gelatin capsules containing also 250 mg dextrose on male volunteers suffering from BPH, preliminary results showed an immediate improvement in urinary flow in some of the patients.

Experiment 3

The impact of exogenously administered melatonin on central melatonin binding sites and serum testosterone in aged male rats was investigated. Thus, 23-month old male rats were treated with melatonin via the drinking water for 30 days. This melatonin supplementation in the aged rat markedly increased melatonin binding sites in the hypothalamus, medulla-pons, thalamus and cortex, and attenuated a suppressive effect of testosterone on melatonin binding sites in steroid-dependent areas (hypothalamus and hippocampus). Serum testosterone levels in the melatonin treated animals did not significantly differ from the values in untreated controls.

Experiment 4

The effects on 8–10 month old adult rats, of long term (~18 months) administration of melatonin via the drinking water (4 mg./l.), on the survival, on central melatonin binding sites, and on serum testosterone, were investigated. Melatonin supplementation markedly increased the number of rats surviving at the age of 24–29 months. In more detail, only 8 of a control group of 16 animals survived at age 26–28 months, and 7 at age 27–29 months, whereas 13 of a melatonin-treated group of 15 animals survived at age 26–28 months and these continued to live at age 27–29 months, when the experiment was terminated by sacrifice of the animals. The significance of the difference in survival was P=0.01 according to two by two Pearson's Chi square test. In addition, the melatonin-treated animals either did not suffer from pneumonia, or had only very weak symptoms; in the control group, 5 of the 7 survivors had severe pneumonia. Melatonin supplementation significantly increased melatonin binding sites in the medulla-pons and hypothalamus in aged rats, and the circadian variations in melatonin binding areas were still evident despite the old age of the animals. Serum testosterone levels in the melatonin treated animals was significantly higher than the values in the untreated controls.

The results of Experiments 3 and 4 demonstrate the advantages of long term melatonin treatment beginning prior to the derangement of the circadian system in the aged, compared with merely short-term treatment in the aged.

Experiment 5

The effects of daily injections over a 14-day period, of the short-term acting benzodiazepine oxazepam, on melatonin binding sites in the rat brain, in both presence and absence of the pineal gland, were investigated. In sham-operated rats specific binding of $^{125}$I-melatonin in all brain areas investigated, exhibited clear diurnal variations. However, the densities of binding sites in these brain areas were higher at midnight (i.e. 19 h after lights-on) in the oxazepam-treated, against the peak at 13 hours after lights-on recorded in the untreated rats. In the pinealectomized rats, melatonin binding in the hypothalamus, hippocampus and medulla-pons, also exhibited clear diurnal variations but phase-shifted as compared to intact or sham operated controls; the densities of binding sites in these brain areas were lower at 13 hours after lights-on than at other times of the day. Daily oxazepam injections decreased melatonin binding sites at 19 hours after lights-on but did not significantly effect the binding at other times of the day.

Melatonin administration via the drinking water had no effect on $^{125}$I-melatonin binding in the various brain areas of the pinealectomized rats at any of the times recorded. In the sham-operated rats, melatonin administration led to a decrease in $^{125}$I-melatonin binding recorded at 13 hours after lights-on in the hippocampus and midbrain.

These results indicate that (a) the diurnal variations in $^{125}$I-melatonin binding sites in the rat brain are not generated by the pineal gland; (b) oxazepam modifies the diurnal variations in $^{125}$I-melatonin binding sites in the rat brain in the presence of the pineal gland and is less effective in its absence; (c) in absence of the pineal gland, the diurnal rhythms of melatonin binding sites in the rat brain are not synchronized with the circadian clock; (d) supplementation of melatonin to pinealectomized rats via the drinking water does not reverse the phase advance of the rhythm in $^{125}$I-melatonin binding.

Preparation and Release Profile of Formulations (a) There were compressed in a 7 mm cylindrical punch at 2.5 tons, after dry mixing of the powdered materials, namely 2 mg/tablet melatonin (Biosynth Co., Switzerland) and acrylic resin carrier (Rohm Pharma), which was Eudragit RS100 (formulation SR-Ms) or Eudragit RSPO (formulation SR-Mf), besides other components as noted: formulation SR-Ms: Eudragit RS100 48.8%, lactose 50%, melatonin 1.2%; formulation SR-Mf: Eudragit RSPO 35.3%, lactose 16.7%, calcium hydrogen phosphate 41.4%, talc 1.3%, magnesium stearate 4%, melatonin 1.3%. SR-Ms and SR-Mf are sustained release formulations.

A conventional dosage form (RM) was prepared similarly to formulation SR-Mf, but using lactose in place of Eudragit as carrier.

(b) The potential release profile of the tablets prepared as described in paragraph (a), was first investigated by in vitro dissolution of melatonin therefrom in distilled water at 37° C. The results in Table A show the % of the melatonin content (mean value of 6 tablets) which has dissolved at the stated intervals of time.

TABLE A

| Time(hours) | 1 | 2 | 4 | 6 | 8 | 10 |
|---|---|---|---|---|---|---|
| melatonin (%) released from: | | | | | | |
| SR-Ms | 12 | 29 | 62 | 84 | 90 | 100 |
| SR-Mf | 32 | 51 | 76 | 88 | 100 | |
| RM | 93 | 96 | 100 | | | |

(c) The in vivo profile of the SR-Mf tablets prepared as described in paragraph (a), was investigated by oral administration twice to a healthy male (age 36) at 10 a.m., i.e. when circulating melatonin levels are undetectable. The amount of melatonin released in vivo was determined by radioimmunoassay of its major metabolite, 6-sulfatoxymelatonin, in the urine. The amount of urinary 6-sulfatoxymelatonin closely reflects the blood level of the hormone. The results in Table B show the melatonin determined as a % of the total melatonin administered (mean value of 2 tablets).

TABLE B

| In vivo release of melatonin from SR-Mf | | | | | | |
|---|---|---|---|---|---|---|
| Time(hours) | 1 | 2 | 4 | 6 | 8 | 10 |
| % release at intervals | 10.7 | 25.7 | 40.6 | 14.0 | 7.0 | 1.9 |
| cumulative release % | 10.7 | 36.4 | 77.0 | 91.0 | 98.0 | 99.9 |

(d) The data in Table B show that it is possible to make a pharmaceutical formulation which simulates the release of melatonin in the human body according to the normal human endogenous melatonin plasma profile. It is noted that the release of melatonin in vitro, illustrated in Table A, provides only an approximate indication of the in vivo release profile due to the known phenomenon of the active compound being absorbed by the tissues in the early stages of release.

It may be noted that the amount of melatonin in the sustained release formulations may be changed e.g. to 0.5, 1 or 5 mg/tablet, without affecting the release pattern found for the tablets containing 2 mg/tablet melatonin.

Details of clinical trials will be set forth in the following Examples, in which the sustained release formulation means a formulation containing the components and having the characteristics of the SR-Mf formulation described above.

EXAMPLE I

Blood tests on a male patient born in 1942, at the time of admission to a urology clinic early in 1992, showed total acid phosphatase 5.3 IU/1, prostatic acid phosphatase 2.7 IU/1 (normal range 0–2.5 IU/ml) and prostate specific antigen (PSA) 7.49 mg/ml (normal range 0–4 mg/ml). Thus, the patient's PSA level was elevated, and his prostatic acid phosphatase level was slightly above normal. Ultrasonographic scanning revealed an enlarged hypertrophic prostate gland, estimated weight 55 g. Residual bladder urine volume retained after two attempts to empty the bladder was found to be 100 ml. Diagnosis after needle biopsy was benign prostate hypertrophy.

The patient began taking 0.5 mg melatonin in the sustained release form daily at 21:00–22:00 hours on Feb. 1, 1992; on a continuing basis, i.e. medication was continued essentially indefinitely. There appeared to be a subjective improvement in urinary flow 6 days after initiation of this treatment. Examination of the patient by ultrasonographic scanning on Oct. 22, 1992, showed no change in estimated size of the prostate gland (55 g), however, residual bladder urine volume retained after two attempts to empty the bladder was zero; at the same time, the measured PSA level in the blood had decreased to 6.4 mg/ml. By Jun. 6, 1993, the measured PSA level in the blood had further decreased to 6.04 mg/ml.

Progressive decrease of the PSA level during continuing administration of melatonin suggests that no further enlargement of the prostate gland occurred during this period. While involution of the gland may also have occurred, change in size may take a long time to become evident.

EXAMPLE II

The effect of melatonin on ultrastructural morphology of the human prostate was examined, by daily administration (in the evening) of 5 mg melatonin in sustained release form to five BPH patients, for a 30-day period prior to prostatectomy. Specimens from the prostate glands removed from the treated patients, and from control untreated patients of the same status, were fixed in glutaraldehyde immediately after the excision, embedded in "Epon" and analyzed by electron microscopy. The results showed evidence for secretion of fresh collagen bundles in the specimens from treated patients only, and thus suggests that the mechanism for secretion of proteins from prostate cells has been influenced by the treatment with melatonin.

EXAMPLE III

In a clinical trial which commenced in April, 1993, 23 BPH patients were recruited and divided into two groups, one group receiving 5 mg melatonin in a sustained release formulation and the other group 50 mg melatonin in a fast release formulation, these dosages being given daily, in the evening. One patient withdrew from the study after 7 days of treatment. All other patients reported subjective improvement of urinary flow, and additionally 8 (randomized) patients reported an urge to sleep two hours after taking the tablet (which accords with the inventor's separate studies on the effect of melatonin on sleep in the elderly). Up to August, 1993, 6 patients finished 3 months' treatment with melatonin, and the remainder had 1–2 months treatment. All patients will continue the treatment with melatonin until 6 months is completed.

In the patients who had completed 3 months' treatment, there was no further enlargement of the prostate gland (3 months is generally too short a time to determine whether any significant decrease in size of the prostate had occurred). Their blood testosterone and prolactin concentrations showed no change, suggesting that testicular function is not impaired. A much higher than usual 6-sulfatoxymelatonin concentration in the urine provided confirmation that the patients took the tablets. In agreement with the results in Example I, above, there was an approximately 10% reproducible decrease in the PSA level in all these patients, suggesting that the prostate epithelial cells have decreased or have stopped growing.

While particular embodiments of the invention have been particularly described hereinabove, it will be appreciated that the present invention is not limited thereto, since, as will be readily apparent to skilled persons, many variations and modifications can be made. Such variations and modifications which have not been detailed herein are deemed to be the obvious equivalents of the present invention. For example, the optional use of growth hormones according to the present invention does not exclude the similar optional use of substances which are generally considered to be growth factors rather than growth hormones. Moreover, analogs of melatonin which substantially imitate the function of melatonin in the human body are deemed to be obvious chemical equivalents of melatonin. The essential concept, spirit and scope of the present invention will be better understood in the light of the claims which follow.

What is claimed is:

1. A method for treating benign prostatic hyperplasia (BPH) in male humans, which comprises administering to a male human in need of such treatment an effective BPH treating amount of melatonin within the range of from 1 ng to 80 mg, wherein said melatonin is administered in combination with a therapeutically effective amount of an antiestrogen.

2. A method for treating benign prostatic hyperplasia (BPH) in a human male which comprises administering to a human male in need of such treatment a therapeutically effective amount of melatonin in combination with a therapeutically effective amount of an antiestrogen.

3. A method according to claim 2, wherein an effective BPH treating amount of melatonin is administered according to a profile which simulates the profile in plasma of a human having a normal endogenous melatonin profile.

4. A method in accordance with claim 2, wherein said administration is oral, parenteral, rectal or transdermal.

* * * * *